United States Patent
Sugahara et al.

(10) Patent No.: US 9,820,714 B2
(45) Date of Patent: Nov. 21, 2017

(54) RADIOGRAPHIC IMAGING SYSTEM, RADIOGRAPHIC IMAGING METHOD AND NON-TRANSITORY RECORDING MEDIUM

(71) Applicant: FUJIFILM Corporation, Tokyo (JP)

(72) Inventors: Masataka Sugahara, Kanagawa (JP); Ayako Muramoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 210 days.

(21) Appl. No.: 14/717,924

(22) Filed: May 20, 2015

(65) Prior Publication Data

US 2015/0250440 A1  Sep. 10, 2015

Related U.S. Application Data

(63) Continuation of application No. PCT/JP2013/081245, filed on Nov. 20, 2013.

(30) Foreign Application Priority Data

Nov. 22, 2012 (JP) .................... 2012-256310

(51) Int. Cl.
A61B 6/04 (2006.01)
A61B 6/00 (2006.01)

(52) U.S. Cl.
CPC .............. A61B 6/542 (2013.01); A61B 6/502 (2013.01); A61B 6/544 (2013.01); A61B 6/0414 (2013.01);
(Continued)

(58) Field of Classification Search
CPC .......... A61B 17/12022; A61B 17/1214; A61B 17/12059; A61B 17/12068; A61B 6/0414; A61B 6/4035; A61B 6/405; A61B 6/461; A61B 6/502; A61B 6/542; A61B 6/544; A61B 6/545; A61B 6/583; A61B 6/4233; A61B 6/488; A61B 6/00; A61B 6/032; A61B 6/4291; A61B 6/4441; A61B 6/463; A61B 6/547; A61B 6/548; A61B 6/5258;
(Continued)

(56) References Cited

U.S. PATENT DOCUMENTS

| | | | | |
|---|---|---|---|---|
| 4,763,343 | A | * | 8/1988 | Yanaki ................... A61B 6/502 378/110 |
| 2004/0086076 | A1 | | 5/2004 | Nagaoka et al. |
| 2004/0101105 | A1 | | 5/2004 | Segawa et al. |

FOREIGN PATENT DOCUMENTS

| | | |
|---|---|---|
| JP | H06-304162 A | 11/1994 |
| JP | 2002-263097 A | 9/2002 |

(Continued)

OTHER PUBLICATIONS

International Search Report (ISR) (PCT Form PCT/ISA/210), in PCT/JP2013/081245, dated Dec. 17, 2013.
(Continued)

Primary Examiner — Irakli Kiknadze
(74) Attorney, Agent, or Firm — McGinn IP Law Group PLLC (57) ABSTRACT

An estimated exposure dose calculator calculates an estimated exposure dose, which is an estimate of an exposure dose of a subject by irradiation of radiation, on the basis of the image capturing conditions after the image capturing conditions are set and prior to the radiation imaging. An exposure dose output unit outputs the calculated estimated exposure dose to the outside.

6 Claims, 3 Drawing Sheets

(52) U.S. Cl.
CPC .............. *A61B 6/405* (2013.01); *A61B 6/4035* (2013.01); *A61B 6/461* (2013.01); *A61B 6/545* (2013.01)

(58) Field of Classification Search
CPC ...... A61B 6/585; A61B 6/025; C07K 14/415; C12N 15/8247
USPC .......... 382/130, 131, 132; 378/4, 37, 21, 20, 378/110, 112, 95
See application file for complete search history.

(56) References Cited

FOREIGN PATENT DOCUMENTS

| | | |
|---|---|---|
| JP | 2004-173924 A | 6/2004 |
| JP | 2009-100926 A | 5/2009 |
| JP | 2010-167165 A | 8/2010 |
| WO | WO 2012/120886 A1 | 9/2012 |
| WO | WO 2012/127819 A1 | 9/2012 |

OTHER PUBLICATIONS

PCT/ISA/237
Japanese Office Action dated Feb. 9, 2016 with an English translation thereof.
Japanese Office Action dated Aug. 30, 2016 with an English Translation thereof.
European Search Report dated Nov. 4, 2015.

* cited by examiner

FIG. 3B ical field

RADIOGRAPHIC IMAGING SYSTEM, RADIOGRAPHIC IMAGING METHOD AND NON-TRANSITORY RECORDING MEDIUM

CROSS-REFERENCE TO RELATED APPLICATIONS AND PRIORITY CLAIM

This application is a Continuation of International Application No. PCT/JP2013/081245 filed on Nov. 20, 2013, which was published under PCT Article 21(2) in Japanese, which is based upon and claims the benefit of priority from Japanese Patent Application No. 2012-256310 filed on Nov. 22, 2012, the contents all of which are incorporated herein by reference.

TECHNICAL FIELD

The present invention relates to a radiographic image capturing system (imaging system) and a radiographic image capturing method (imaging method), which perform a radiographic image capturing process by applying radiation from a radiation source to a subject according to image capturing conditions, and by converting radiation that has passed through the subject into a radiographic image by a radiation detector. The present invention also relates to a non-transitory recording medium storing a program therein for performing such a radiographic image capturing process.

BACKGROUND ART

Heretofore, it has been customary to capture a radiographic image of a breast of a subject, for example, in the following manner. First, the breast is compressed and then image capturing conditions are set, which represent a tube voltage of a radiation source, an mAs value (the product of the tube current and an irradiation time for the radiation), the thickness of the compressed breast, and the types of a target and a filter that make up the radiation source. Then, the radiation source applies radiation to the compressed breast according to the set image capturing conditions. Radiation that has passed through the breast is converted into a radiographic image by a radiation detector. Thereafter, the image capturing conditions that were used during capturing of the radiographic image are displayed as an exposure dose record of the subject on a display device.

In a case where the doctor or radiological technician manually sets image capturing conditions and performs a radiographic image capturing process (manual radiographic image capturing process) according to the set image capturing conditions, without enabling an AEC (automatic exposure control) function, the doctor or radiological technician may set image capturing conditions in terms of image quality (contrast) of a radiographic image to be captured, without regard to the exposure dose applied to the subject. As a result, the subject may undergo a meaningless exposure to radiation.

According to the radiographic image capturing process of the conventional technique, value has been placed only on the image quality of radiographic images to be captured, and there has been a lack of interest in the exposure dose applied to the subject. In recent years, radiographic image capturing techniques for reducing the exposure dose applied to the subject have been disclosed in Japanese Laid-Open Patent Publication No. 2002-263097, Japanese Laid-Open Patent Publication No. 2004-173924, and Japanese Laid-Open Patent Publication No. 2010-167165.

SUMMARY OF INVENTION

However, even with the techniques disclosed in the above publications, a radiographic image capturing process is carried out on the subject before the image capturing conditions are set, in order to determine image capturing conditions. More specifically, according to the techniques disclosed in the above publications, two radiographic image capturing processes are performed in order to acquire a desired radiographic image (i.e., a first radiographic image capturing process for determining image capturing conditions, and a second radiographic image capturing process for acquiring a radiographic image). Consequently, since the first radiographic image capturing process is added, the accumulated exposure dose applied to the subject can be expected to increase, despite the fact that the techniques disclosed in the above publications are aimed at reducing the exposure dose applied to the subject.

Further, the above publications do not disclose that, in a case where a doctor or radiological technician manually sets image capturing conditions, the doctor or radiological technician is prompted to recognize, prior to performing a radiographic image capturing process on a subject, the exposure dose applied to the subject at the time that radiation is applied to the subject under the manually-set image capturing conditions.

The present invention has been devised in order to solve the aforementioned problems. An object of the present invention is to provide a radiographic image capturing system, a radiographic image capturing method, and a non-transitory recording medium, which are capable of prompting a doctor or radiological technician to recognize beforehand an exposure dose applied to a subject in a radiographic image capturing process (manual radiographic image capturing process), which is carried out on the subject under image capturing conditions that are manually set by the doctor or radiological technician.

A further object of the present invention is to provide a radiographic image capturing system, a radiographic image capturing method, and a non-transitory recording medium, which are capable of prompting a doctor or radiological technician to set proper image capturing conditions, so as to avoid a meaningless exposure dose by having the doctor or radiological technician recognize the exposure dose applied to the subject before a manual radiographic image capturing process is carried out on the subject.

The present invention is concerned with a radiographic image capturing system for carrying out a radiographic image capturing process by setting a tube voltage of a radiation source, an mAs value, types of a target and a filter that make up the radiation source, and information concerning a subject, as image capturing conditions, by an image capturing condition setting section, thereafter applying radiation from the radiation source to the subject according to the image capturing conditions, and converting the radiation that has passed through the subject into a radiographic image by a radiation detector.

The radiographic image capturing system includes an estimated exposure dose calculator configured to calculate an estimated exposure dose representing an estimated value of a dose to which the subject will be exposed by applying radiation to the subject, on the basis of the image capturing conditions after the image capturing conditions have been set and before the radiographic image capturing process is carried out, and an exposure dose output unit configured to output, to outside, the estimated exposure dose that has been calculated.

The present invention also is concerned with a radiographic image capturing method for carrying out a radiographic image capturing process by setting a tube voltage of a radiation source, an mAs value, types of a target and a filter that make up the radiation source, and information concerning a subject, as image capturing conditions, thereafter applying radiation from the radiation source to the subject according to the image capturing conditions, and converting the radiation that has passed through the subject into a radiographic image by a radiation detector.

The radiographic image capturing method includes a first step of calculating an estimated exposure dose representing an estimated value of a dose to which the subject will be exposed by applying radiation to the subject, on the basis of the image capturing conditions after the image capturing conditions have been set and before the radiographic image capturing process is carried out, and a second step of outputting, to outside, the estimated exposure dose that has been calculated.

The present invention is further concerned with a non-transitory recording medium storing a program therein.

The program that is stored in the non-transitory recording medium enables a computer to function as:

an image capturing condition setting section configured to set a tube voltage of a radiation source, an mAs value, types of a target and a filter that make up the radiation source, and information concerning a subject, as image capturing conditions;

an estimated exposure dose calculator configured to calculate an estimated exposure dose representing an estimated value of a dose to which the subject will be exposed by applying radiation to the subject, on the basis of the image capturing conditions before a radiographic image capturing process is carried out for applying radiation from the radiation source to the subject according to the image capturing conditions after the image capturing conditions have been set, and converting radiation that has passed through the subject into a radiographic image by a radiation detector; and an exposure dose output unit configured to output, to outside, the estimated exposure dose that has been calculated.

According to the present invention, after the image capturing conditions have been set and before the radiographic image capturing process is carried out, the estimated exposure dose is calculated, and the estimated exposure dose that has been calculated is output to outside. On the basis of the output results, the doctor or radiological technician can recognize in advance how much of an exposure dose the subject will be subjected to during the radiographic image capturing process (manual radiographic image capturing process) performed according to the image capturing conditions. Thus, the doctor or radiological technician can appropriately set image capturing conditions even manually, so as to prevent the subject from being subjected to a meaningless exposure dose.

As a result, it is possible to set image capturing conditions in order to maintain the image quality (contrast) of a radiographic image while avoiding a meaningless exposure dose with respect to the subject. Since the estimated exposure dose is output prior to a radiographic image capturing process, it is not necessary to carry out a radiographic image capturing process for determining image capturing conditions, thereby reducing the accumulated exposure dose applied to the subject.

The present invention may include the following additional features [1] through [7]:

[1] The radiographic image capturing system may further include an estimated exposure dose adjuster configured to adjust the estimated exposure dose. In a case where the estimated exposure dose, which is calculated by the estimated exposure dose calculator, is relatively large, for example, it is possible for the estimated exposure dose adjuster to adjust the estimated exposure dose to a lower value. Further, it is possible to reset image capturing conditions by referring to the estimated exposure dose that has been adjusted.

[2] The radiographic image capturing system may further include an image capturing condition adjuster configured to adjust the image capturing conditions.

In this case, in a case where the estimated exposure dose adjuster adjusts the estimated exposure dose, the image capturing condition adjuster automatically adjusts the image capturing conditions on the basis of the estimated exposure dose that has been adjusted. Alternatively, in a case where the image capturing condition adjuster adjusts the image capturing conditions, the estimated exposure dose adjuster automatically adjusts the estimated exposure dose on the basis of the image capturing conditions that have been adjusted.

In either case, since the image capturing conditions or the estimated exposure dose is automatically adjusted in terms of the exposure dose applied to the subject, the exposure dose applied to the subject can be reduced efficiently, and at the same time, the image quality of the radiographic image can be maintained.

[3] The image capturing condition adjuster preferably adjusts the image capturing conditions by changing the mAs value in a state where the tube voltage is set to a fixed value. The tube voltage is a factor that determines the image quality (contrast) of the radiographic image. Therefore, assuming that the image capturing conditions are adjusted by changing the mAs value in a state where the tube voltage is set to a fixed value, the exposure dose applied to the subject can be reduced without causing a reduction in the image quality of the radiographic image.

[4] The radiographic image capturing system may further include a table representing a relationship between estimated exposure doses, tube voltages, and mAs values. In this case, by referring to the table, the image capturing condition adjuster may specify an mAs value depending on the estimated exposure dose calculated by the estimated exposure dose calculator, or may specify an mAs value depending on the estimated exposure dose adjusted by the estimated exposure dose adjuster. Consequently, the image capturing conditions (mAs value) can be adjusted efficiently.

[5] The exposure dose output unit may output the estimated exposure dose that has been adjusted by the estimated exposure dose adjuster, so that the doctor or radiological technician can recognize the estimated exposure dose that has been adjusted, prior to the radiographic image capturing process.

[6] In a case where the exposure dose output unit includes a display unit configured to display the estimated exposure dose and the image capturing conditions, by viewing the content displayed on the display unit, the doctor or radiological technician can easily recognize the estimated exposure dose and the image capturing conditions prior to the radiographic image capturing process.

[7] The radiographic image capturing system further includes a radiographic image capturing apparatus including the radiation source and the radiation detector, and a control apparatus configured to control the radiographic image capturing apparatus, the control apparatus including the image capturing condition setting section, the estimated exposure dose calculator, and the exposure dose output unit.

In this case, the radiographic image capturing apparatus further includes an image capturing table on which a breast of the subject is placed, the image capturing table housing the radiation detector therein, a compression member configured to compress the breast by displacement of the compression member toward the image capturing table, and a compressed thickness measurement unit configured to measure the thickness of the breast that is compressed by the compression member.

Further, the radiation source applies radiation to the breast that has been compressed, and the radiation detector converts the radiation that has passed through the breast into the radiographic image. Among the image capturing conditions, the information concerning the subject represents the thickness of the breast of the subject, and the estimated exposure dose represents an estimated value of an average mammary gland dose applied to the breast.

The present invention, as applied to a mammographic apparatus, is effective both at reducing an exposure dose applied to the breast, and maintaining the image quality of a radiographic image of the breast.

The aforementioned objects and other objects, characteristics, and advantages of the present invention will become more apparent from the following descriptions of preferred embodiments, taken in conjunction with the accompanying drawings.

DESCRIPTION OF EMBODIMENTS

A radiographic image capturing system according to a preferred embodiment of the present invention will be described below with reference to the accompanying drawings, in relation to a radiographic image capturing method and a non-transitory recording medium.

[Configuration of Radiographic Image Capturing System]

Figure 1:
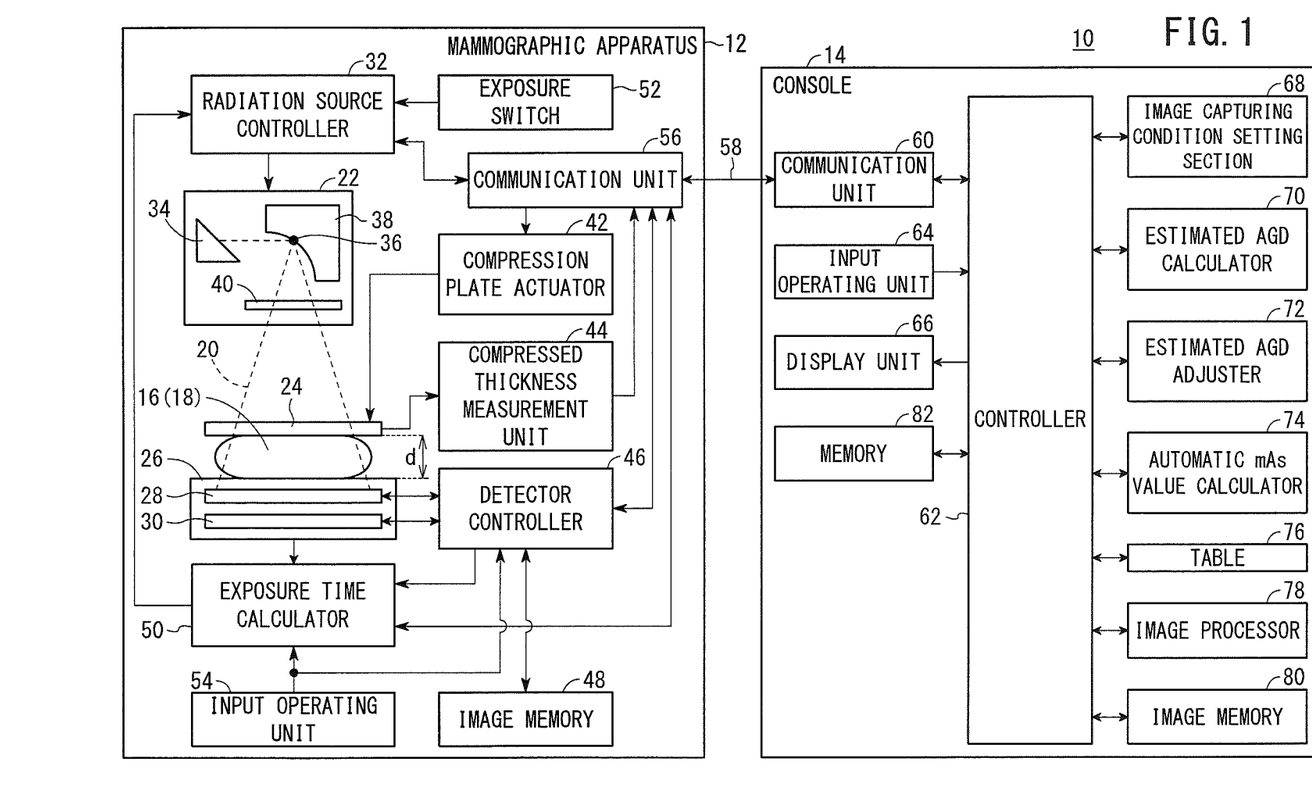
FIG. 1 is a block diagram of a radiographic image capturing system according to an embodiment of the present invention.

As shown in FIG. 1, the radiographic image capturing system 10 according to the present embodiment comprises a mammographic apparatus 12 as a radiographic image capturing apparatus, and a console 14 as a control apparatus (computer) for controlling the mammographic apparatus 12.

The mammographic apparatus 12 acquires a radiographic image of a breast 18 of a subject 16 by applying radiation 20 to the breast 18.

More specifically, the mammographic apparatus 12 includes a radiation source 22 for emitting radiation 20, an image capturing table 26 on which a breast 18 of the subject is placed, and a compression plate (compression member) 24 disposed between the radiation source 22 and the image capturing table 26, and which is displaceable toward the image capturing table 26 for compressing and holding the breast 18 in cooperation with the image capturing table 26.

The image capturing table 26 houses therein a solid-state detector (radiation detector) 28 for converting radiation 20 that has passed through the breast 18 into a radiographic image, and an AEC sensor 30 disposed behind the solid-state detector 28 with respect to the direction in which radiation 20 is applied.

The radiation source 22 comprises a thermionic-emission-type X-ray source that is controlled by a radiation source controller 32. More specifically, in the radiation source 22, there are accommodated a cathode 34 for emitting thermions, a target 38 serving as an anode for emitting radiation such as X-rays or the like from a focus 36 as a result of collision of thermions, which are emitted from the cathode 34, with the target 38, and a filter 40 through which radiation of a desired quality is passed, which serves as radiation 20, from among the radiation that is emitted from the target 38.

According to the present embodiment, a combination of the target 38 and the filter 40 may be represented by Mo/Mo, Mo/Rh, Rh/Rh, Rh/Al, W/Rh, or W/Al, for example, which indicates the "type of target 38"/"type of filter 40".

The mammographic apparatus 12 also includes a compression plate actuator 42, a compressed thickness measurement unit 44, a detector controller 46, an image memory 48, an exposure time calculator 50, an exposure switch 52, an input operating unit 54, and a communication unit 56.

The compression plate actuator 42 moves the compression plate 24, which is disposed between the radiation source 22 and the image capturing table 26, toward and away from the image capturing table 26. Upon compression of the breast 18 between the compression plate 24 and the image capturing table 26, the compressed thickness measurement unit 44 measures the position of the compression plate 24, which represents the thickness (compressed thickness d) of the compressed breast 18. The compressed thickness measurement unit 44 also measures the pressure (compressing pressure P) that is applied from the compression plate 24 to the breast 18.

The detector controller 46 controls the solid-state detector 28 to acquire a radiographic image from the solid-state detector 28, and stores the acquired radiographic image in the image memory 48. The detector controller 46 also is capable of controlling the AEC sensor 30 and the exposure time calculator 50 in order to perform an AEC function, which is of a known nature.

More specifically, a pre-exposure process is performed to apply radiation 20 of a relatively low dose from the radiation source 22 to the breast 18, with the object of setting image capturing conditions for a radiographic image capturing process to be carried out on the breast 18, whereupon the AEC sensor 30 detects the exposure dose of radiation 20 that has passed through the breast 18 and the solid-state detector 28. Based on the detected radiation dose per unit time at a position of a mammary gland of the breast 18, the exposure time calculator 50 calculates an appropriate exposure time for the radiation 20 from the radiation source 22. Thereafter, the calculated exposure time is output to the radiation source controller 32 as an irradiation time for the radiation 20 in a main exposure process for acquiring a radiographic image of the breast 18.

According to the present embodiment, the AEC function is disabled so that the pre-exposure process is not carried out. More specifically, according to the present embodiment, image capturing conditions are set on the basis of an instruction from the doctor or radiological technician. Further, a manual image capturing process (radiographic image capturing process) for applying radiation 20 to the breast 18 is carried out according to the set image capturing conditions. The manual image capturing process according to the present embodiment corresponds to the above-described main image capturing process. In the present embodiment, therefore, detailed description of the AEC function is omitted.

The exposure switch 52 is operated by the doctor or radiological technician. In a case where the doctor or radiological technician presses the exposure switch 52, the radiation source controller 32 energizes the radiation source 22 in order to enable the radiation source 22 to initiate emission of radiation 20.

The input operating unit 54 is an input operating unit such as an operating button or a touch panel provided on the mammographic apparatus 12. In response to an operation carried out on the input operating unit 54 by the doctor or radiological technician, the detector controller 46 controls the AEC sensor 30 and the exposure time calculator 50, so as to enable (turn on) or disable (turn off) the AEC function. In response to an operation carried out on the input operating unit 54 by the doctor or radiological technician, the compression plate actuator 42 moves the compression plate 24 in order to compress the breast 18 that has been placed on the image capturing table 26, or to release the breast 18 from a compressed state.

The communication unit 56 sends various signals and information to or receives various signals and information from the console 14 through a communication line 58. For example, the communication unit 56 may send a radiographic image, which the detector controller 46 has read from the image memory 48, to the console 14 through a communication line 58. The communication unit 56 may also send the compressed thickness d of the breast 18 and the compressing pressure P applied to the breast 18, which have been measured by the thickness measurement unit 44, to the console 14 through the communication line 58. The communication unit 56 receives image capturing conditions for a radiographic image capturing process, which is to be performed on the breast 18, from the console 14 through the communication line 58, and outputs the received image capturing conditions to the radiation source controller 32.

As shown in FIG. 1, the mammographic apparatus 12 and the console 14 communicate with each other over a wired communication link provided by the communication line 58. However, the present embodiment is not limited to such illustrated details, insofar as signals and information may be exchanged between the mammographic apparatus 12 and the console 14 according to a known communication method such as a wireless communication link, an infrared communication link, or the like.

The console 14 includes a communication unit 60, a controller 62, an input operating unit 64, a display unit (exposure dose output unit) 66, an image capturing condition setting section 68, an estimated AGD calculator (estimated exposure dose calculator) 70, an estimated AGD adjuster (estimated exposure dose adjuster) 72, an automatic mAs value calculator (image capturing condition adjuster) 74, a table 76, an image processor 78, an image memory 80, and a memory (non-transitory recording medium) 82.

The controller 62 controls various components of the console 14 by reading and executing programs stored in the memory 82, which comprises a non-transitory recording medium such as a ROM, a hard disk, a CD-ROM, or the like.

The image capturing condition setting section 68 sets image capturing conditions in relation to a radiographic image capturing process for applying radiation 20 from the radiation source 22 to the breast 18, converting radiation 20 that has passed through the breast 18 into a radiographic image with the solid-state detector 28, and acquiring a radiographic image. The image capturing conditions include a tube voltage of the radiation source 22, an mAs value (a product of a tube current and an irradiation time for the radiation 20), types of the target 38 and the filter 40 that make up the radiation source 22, and the compressed thickness d of the breast 18, which represents information concerning the subject 16.

The image capturing conditions are set in response to an operation carried out by the doctor or radiological technician on the input operating unit 64, which may be an operating button or an input operating unit of a touch panel, for example. In other words, the image capturing conditions are entered manually by the doctor or radiological technician, whereby the image capturing conditions are set in the image capturing condition setting section 68.

After the image capturing conditions have been set, the estimated AGD calculator 70 calculates an estimated exposure dose representing an estimated value of the dose to which (the breast 18 of) the subject 16 will be exposed by applying radiation 20 to the breast 18 according to the image capturing conditions, on the basis of the image capturing conditions set in the image capturing condition setting section 68, and before a radiographic image capturing process actually is carried out on the breast 18. More specifically, the estimated AGD calculator 70 estimates an average mammary gland dose (AGD) based on the image capturing conditions, and calculates the estimated level of the AGD (hereinafter referred to as an "estimated AGD") as an estimated exposure dose.

The estimated AGD represents an average value, which is estimated according to the image capturing conditions, of the radiation dose that is absorbed by the mammary gland of the breast 18 while the breast 18 is uniformly compressed between the compression plate 24 and the image capturing table 26. The estimated AGD is expressed by the following equation (1):

$$(\text{Estimated AGD}) = K \times g \times c \times s \tag{1}$$

where K [mGy] represents a skin surface dose (dose of radiation 20 applied to the breast 18), "g" represents a conversion coefficient for a mammary gland content rate of 50%, "c" represents a corrective coefficient for a mammary gland content rate that deviates from 50%, and "s" represents a corrective coefficient for the materials that constitute the target 38 and the filter 40. Thus, according to equation (1), the estimated AGD calculator 70 can calculate an estimated AGD based on the image capturing conditions.

The estimated AGD adjuster 72 adjusts the estimated AGD that was calculated by the estimated AGD calculator 70. For example, in a case where the estimated AGD is higher than a desired dose (i.e., in a case where the exposure dose applied to the breast 18 is high due to the image capturing conditions), the estimated AGD adjuster 72 adjusts the estimated AGD to a lower value.

The automatic mAs value calculator 74 automatically adjusts the mAs value in a state where the tube voltage is set to a fixed value from among the image capturing conditions set by the image capturing condition setting section 68, and updates the image capturing conditions contained in the image capturing condition setting section 68 into changed image capturing conditions. More specifically, the automatic mAs value calculator 74 automatically adjusts the mAs value based on the estimated AGD that was calculated by the estimated AGD calculator 70, or automatically adjusts the mAs value based on the estimated AGD that was adjusted by the estimated AGD adjuster 72. Using the input operating unit 64, in a case where the doctor or radiological technician enters an instruction indicating a change in the image capturing conditions, the automatic mAs value calculator 74 also is capable of adjusting the mAs value depending on such an instruction.

The table 76 stores a table representing a relationship between estimated AGDs, tube voltages, and mAs values. Therefore, by referring to the table 76, the automatic mAs value calculator 74 can read image capturing conditions from the image capturing condition setting section 68, extract the tube voltages and the mAs values from the read image capturing conditions, and specify an mAs value corresponding to the estimated AGD that was calculated by the estimated AGD calculator 70, or the estimated AGD that was adjusted by the estimated AGD adjuster 72, and the tube voltage.

The display unit 66 displays the image capturing conditions and the estimated AGD. More specifically, (1) in a case where image capturing conditions are set in the image capturing condition setting section 68, (2) in a case where the estimated AGD calculator 70 calculates an estimated AGD, (3) in a case where the estimated AGD adjuster 72 adjusts an estimated AGD, or (4) in a case where image capturing conditions are updated by the automatic mAs value calculator 74, the display unit 66 displays the image capturing conditions, which have been set or updated, and the estimated AGD, which has been calculated or adjusted.

Under the control of the controller 62, the communication unit 60 sends the image capturing conditions, which are set or updated in the image capturing condition setting section 68, through the communication line 58 to the communication unit 56 of the mammographic apparatus 12. The communication unit 60 also outputs the compressed thickness d, the compressing pressure P, and the radiographic image, which have been received from the communication unit 56 through the communication line 58, to the controller 62. The controller 62 outputs the compressed thickness d and the compressing pressure P as image capturing conditions to the image capturing condition setting section 68. In addition, the controller 62 stores the radiographic image in the image memory 80.

The image processor 78 performs a prescribed image processing routine on the radiographic image that is stored in the image memory 80, stores the processed radiographic image in the image memory 80, and displays the processed radiographic image on the display unit 66.

[Operations of Radiographic Image Capturing System]

Operations (a radiographic image capturing method) of the radiographic image capturing system 10, which is configured in the foregoing manner, will be described below with reference to FIG. 2 as well as FIG. 1 if necessary.

A case will be described in which, after the AEC function has been turned off, image capturing conditions are set manually by the doctor or radiological technician, the estimated AGD calculator 70 calculates an estimated AGD using the set image capturing conditions, the estimated AGD is displayed on the display unit 66, and thereafter, a radiographic image capturing process (manual radiographic image capturing process) is carried out on the breast 18.

Figure 2:
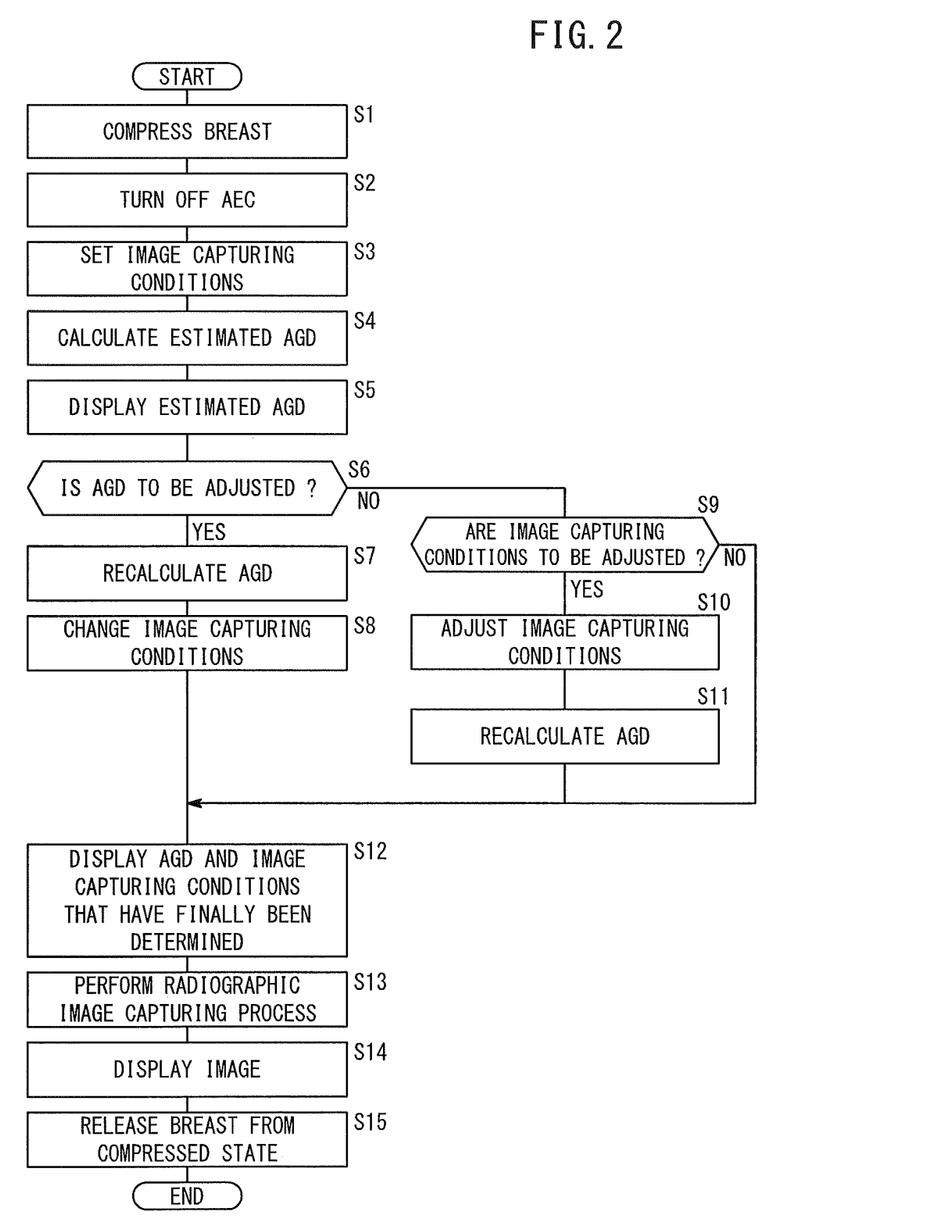
FIG. 2 is a flowchart of an operation sequence of the radiographic image capturing system shown in FIG. 1.

In step S1 of FIG. 2, the doctor or radiological technician places the breast 18 on the image capturing table 26. Next, in response to an operation carried out on the input operating unit 54 by the doctor or radiological technician, the compression plate actuator 42 moves the compression plate 24 toward the image capturing table 26, thereby causing the compression plate 24 and the image capturing table 26 to compress the breast 18. The compressed thickness measurement unit 44 measures a compressed thickness d and a compressing pressure P, and outputs information representing the compressed thickness d and the compressing pressure P, which have been measured, to the communication unit 56. The communication unit 56 sends the information through the communication line 58 to the communication unit 60. Among the information received through the communication unit 60, the controller 62 sets the compressed thickness d in the image capturing condition setting section 68.

In the next step S2, the doctor or radiological technician operates the input operating unit 54 in order to disable the AEC function. Consequently, in accordance with a signal from the input operating unit 54, the detector controller 46 controls the AEC sensor 30 and the exposure time calculator 50 so as not to operate.

In step S3, the doctor or radiological technician operates the input operating unit 64 in order to enter a tube voltage, a tube current, and an irradiation time (mAs value). At this time, the compressed thickness d already is set in the image capturing condition setting section 68. Further, assuming that the target 38 and the filter 40 have been placed in the radiation source 22, the types of the target 38 and the filter 40 are preset in the image capturing condition setting section 68.

Therefore, the image capturing condition setting section 68 sets the tube voltage and the mAs value that have been entered, the compressed thickness d, which has already been set, and the types of the target 38 and the filter 40, as image capturing conditions for a radiographic image capturing process to be performed with respect to the breast 18.

In step S4 (first step), the estimated AGD calculator 70 reads the image capturing conditions that were set in the image capturing condition setting section 68, and calculates an estimated AGD based on the read image capturing conditions according to equation (1). In step S5 (second step), the estimated AGD calculator 70 displays the calculated AGD on the display unit 66.

In step S6, the doctor or radiological technician views the estimated AGD that is displayed on the display unit 66, and considers whether or not to adjust the estimated AGD.

For example, in a case where the estimated AGD represents a large dose on the breast 18, the doctor or radiological technician determines that the estimated AGD is too high (step S6: YES), and operates the input operating unit 64 to set the estimated AGD to a lower value. In this case, the doctor or radiological technician may operate the input operating unit 64 in order to enter a dose value that is lower than the estimated AGD, or to enter an instruction for reducing the high estimated AGD to a lower value.

In the next step S7, according to an instruction from the input operating unit 64, the estimated AGD adjuster 72 adjusts (recalculates) the value of the estimated AGD. In the following step S8, the automatic mAs value calculator 74 reads the image capturing conditions from the image capturing condition setting section 68, and by referring to the table 76, specifies an mAs value that corresponds with the tube voltage from among the read image capturing conditions and the estimated AGD adjusted by the estimated AGD adjuster 72. At this time, the automatic mAs value calculator 74 specifies an mAs value that corresponds with the tube voltage and the estimated AGD in a state where the tube voltage is set to a fixed value. In addition, the automatic mAs value calculator 74 updates the image capturing conditions, which are set in the image capturing condition setting section 68, into new image capturing conditions including the specified mAs value.

In a case where, in step S6, the doctor or radiological technician determines that the estimated AGD does not need to be adjusted (step S6: NO) but that the image capturing conditions should be adjusted (step S9: YES), the doctor or radiological technician operates the input operating unit 64 in order to enter desired image capturing conditions. At this time as well, with respect to the entered image capturing conditions, by referring to the table 76, the automatic mAs value calculator 74 specifies an mAs value depending on the tube voltage, which is set to a fixed value, and the estimated AGD that was calculated by the estimated AGD calculator 70 (step S10). As a result, the automatic mAs value calculator 74 updates the image capturing conditions that are set in the image capturing condition setting section 68 into new image capturing conditions including the specified mAs value. Further, since the image capturing conditions have been updated, in step S11, the estimated AGD calculator 70 recalculates an estimated AGD based on the updated image capturing conditions.

In a case where the doctor or radiological technician, having viewed the estimated AGD displayed on the display unit 66, judges that both the estimated AGD and the image capturing conditions do not need to be adjusted (step S6: NO, step S9: NO), using the input operating unit 64, the doctor or radiological technician enters an instruction indicating that there is no need for adjustment. Based on the entered instruction, the controller 62 controls the various components of the console 14 so as not to execute steps S7, S8, S10, and S11.

As a consequence, in step S12, the controller 62 controls the display unit 66 in order to display the image capturing conditions and the estimated AGD that have finally been determined.

More specifically, in a case where the estimated AGD and the image capturing conditions do not need to be adjusted (step S6: NO, step S9: NO), the controller 62 controls the display unit 66 to display the image capturing conditions, which were initially set in the image capturing condition setting section 68 in step S3, and the estimated AGD, which was calculated in step S4 by the estimated AGD calculator 70.

In a case where the estimated AGD is adjusted in steps S6 and S7, the controller 62 controls the display unit 66 to display the estimated AGD that was recalculated by the estimated AGD adjuster 72 in step S7, and the image capturing conditions that were updated by the image capturing condition setting section 68 in step S8.

In a case where the image capturing conditions are adjusted in steps S10 and S11, the controller 62 controls the display unit 66 to display the image capturing conditions that were updated in step S10 by the image capturing condition setting section 68, and the estimated AGD that was recalculated in step S11 by the estimated AGD adjuster 72.

After the doctor or radiological technician has viewed the content displayed on the display unit 66 (the image capturing conditions and the estimated AGD that have ultimately been determined), then in step S13, the doctor or radiological technician presses the exposure switch 52 in order to initiate the radiographic image capturing process on the breast 18.

The radiation source controller 32 issues a request through the communication unit 56 for the console 14 to transmit image capturing conditions. Based on the transmission request sent from the radiation source controller 32 through the communication line 58 and the communication unit 60, the controller 62 reads the image capturing conditions (i.e., the initially set image capturing conditions or the updated image capturing conditions) that are set in the image capturing condition setting section 68, and sends the read image capturing conditions to the mammographic apparatus 12 through the communication unit 60.

Upon receiving the image capturing conditions through the communication line 58 and the communication unit 56, the radiation source controller 32 energizes the radiation source 22 according to the received image capturing conditions, thereby causing the radiation source 22 to emit radiation 20. Radiation 20 emitted from the radiation source 22 is applied through the compression plate 24 to the breast 18. The emitted radiation 20 passes through the breast 18, and is converted into a radiographic image by the solid-state detector 28 in the image capturing table 26.

The detector controller 46 reads the radiographic image from the solid-state detector 28, and temporarily stores the radiographic image in the image memory 48. Thereafter, the detector controller 46 reads the radiographic image stored in the image memory 48, and sends the radiographic image through the communication unit 56 to the console 14.

The controller 62 receives the radiographic image through the communication line 58 and the communication unit 60, and stores the radiographic image in the image memory 80. The image processor 78 reads the radiographic image that is stored in the image memory 80, and performs a prescribed image processing routine on the read radiographic image. The image processor 78 also displays the processed radiographic image on the display unit 66, and stores the processed radiographic image in the image memory 80 (step S14).

The doctor or radiological technician views the radiographic image displayed on the display unit 66, and confirms that the desired radiographic image has been acquired. Thereafter, the doctor or radiological technician operates the input operating unit 54 to energize the compression plate actuator 42, thereby moving the compression plate 24 toward the radiation source 22. At this time, the breast 18 becomes released from the compressed state (step S15), and the radiographic image capturing process on the breast 18 is brought to an end.

Figure 3A:
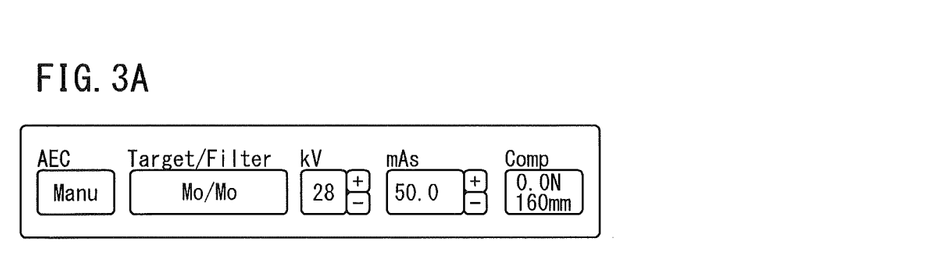
FIG. 3A is a diagram showing content displayed on a screen according to the background art.

FIG. 3A shows the content that is displayed on the screen of the display unit after the radiographic image capturing process on the breast 18 has been completed according to the background art.

According to the background art, in a case where image capturing conditions are set manually by the doctor or radiological technician with the AEC function being disabled, and a radiographic image capturing process (manual radiographic image capturing process) is carried out on the breast 18, after the radiographic image capturing process is completed, the screen of the display unit displays an exposure dose record of the breast 18 that was irradiated with radiation 20. According to the background art, therefore, the doctor or radiological technician is not able to recognize an exposure dose (AGD) applied to the breast 18 in advance of the radiographic image capturing process. In the displayed content shown in FIG. 3A, "AEC Manu" indicates that the AEC function is disabled and that a manual radiographic image capturing process is carried out, "Target/Filter Mo/Mo" indicates that both the target 38 and the filter 40 are made of Mo, "kV" and "mAs" represent a tube voltage and an mAs value, respectively, and "Comp" indicates a compressing pressure P and a compressed thickness d.

Figure 3B:
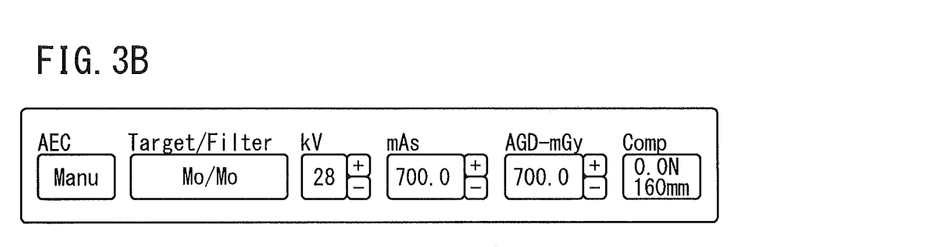
FIG. 3B is a diagram showing content displayed on a screen according to the embodiment.

According to the present embodiment, on the other hand, the display unit 66 is controlled in order to display the content shown in FIG. 3B on the screen thereof in steps S5 and S12 of FIG. 2, before a radiographic image capturing process is carried out. Thus, the doctor or radiological technician is capable of recognizing an exposure dose (AGD) applied to the breast 18 in advance. The displayed content shown in FIG. 3B includes a display field "AGD-mGy" indicating an estimated AGD[mGy], in addition to the display fields shown in FIG. 3A.

Therefore, in a case where the display unit 66 displays the content shown in FIG. 3B on the screen thereof in step S5, by viewing the estimated AGD and the image capturing conditions, the doctor or radiological technician can judge whether or not the processes of steps S6 through S11 should be performed by the console 14. Thus, it is possible to prevent the subject from being subjected to a meaningless exposure to radiation. In a case where the display unit 66 displays the content shown in FIG. 3B on the screen thereof in step S12, by viewing the estimated AGD and the image capturing conditions, the doctor or radiological technician can recognize that the radiographic image capturing process in step S13 will be performed on the breast 18 under such conditions.

Advantages of the Present Embodiment

According to the present embodiment, as described above, after the image capturing conditions have been set and before a radiographic image capturing process is carried out, an estimated AGD is calculated, and the estimated AGD that has been calculated is displayed on the display unit 66. Based on the displayed content, the doctor or radiological technician is capable of recognizing, in advance of the radiographic image capturing process, how much of an exposure dose the breast 18 of the subject 16 will be subjected to during the radiographic image capturing process (manual radiographic image capturing process) performed according to the image capturing conditions. Thus, the doctor or radiological technician can appropriately set the image capturing conditions even manually, so as to prevent the subject 16 from being subjected to a meaningless exposure dose.

As a result, it is possible to set image capturing conditions in order to maintain the image quality (contrast) of a radiographic image while avoiding a meaningless exposure dose with respect to the breast 18. Since the estimated AGD is displayed on the display unit 66 prior to the radiographic image capturing process, it is not necessary to carry out a radiographic image capturing process (pre-exposure process) for determining image capturing conditions, thereby reducing the accumulated exposure dose applied to the subject 16.

Since the console 14 includes the estimated AGD adjuster 72, in a case where the estimated AGD, which is calculated by the estimated AGD calculator 70, is relatively large, for example, it is possible to adjust the estimated AGD to a lower value. As a result, it is possible to reset the image capturing conditions by referring to the estimated AGD that has been adjusted.

Inasmuch as the console 14 includes the automatic mAs value calculator 74, in a case where the estimated AGD adjuster 72 adjusts the estimated AGD, the automatic mAs value calculator 74 automatically adjusts the image capturing conditions on the basis of the estimated AGD that has been adjusted. Alternatively, in a case where the automatic mAs value calculator 74 adjusts the image capturing conditions, the estimated AGD adjuster 72 automatically adjusts the estimated AGD on the basis of the image capturing conditions that have been adjusted.

In either case, since the image capturing conditions or the estimated AGD is automatically adjusted in terms of the exposure dose applied to the breast 18, the exposure dose applied to the breast 18 can be reduced efficiently, and at the same time, the image quality of the radiographic image can be maintained.

More specifically, the automatic mAs value calculator 74 adjusts the image capturing conditions by changing the mAs value in a state where the tube voltage is set to a fixed value. The tube voltage is a factor that determines the image quality (contrast) of the radiographic image. Therefore, assuming that the image capturing conditions are adjusted by changing the mAs value in state where the tube voltage is set to a fixed value, the exposure dose applied to the breast 18 can be reduced without causing a reduction in the image quality of the radiographic image. In other words, the exposure dose applied to the breast 18 is reduced efficiently, while at the same time, the image quality of the radiographic image is maintained by adjusting the image capturing conditions in terms of the exposure dose applied to the breast 18.

Further, the automatic mAs value calculator 74 specifies an mAs value depending on the estimated AGD that was calculated by the estimated AGD calculator 70, or specifies an mAs value depending on the estimated AGD that was adjusted by the estimated AGD adjuster 72 with reference to the table 76. Thus, the mAs value can be adjusted efficiently.

Furthermore, the display unit 66 displays the image capturing conditions, which have been set or updated in the image capturing condition setting section 68, the estimated AGD, which has been calculated by the estimated AGD calculator 70, and the estimated AGD, which has been adjusted by the estimated AGD adjuster 72. Therefore, by viewing the displayed content before the radiographic image capturing process is carried out, the doctor or radiological technician can easily recognize the image capturing conditions that have been set or updated, and the estimated AGD that has been calculated or adjusted.

In the above description, the console 14 is capable of adjusting the mAs value and the estimated AGD. However, the present embodiment is not limited to this description, and it is possible to adjust the tube voltage insofar as the image quality of the radiographic image is not lowered. Furthermore, since the mAs value represents the product of the tube current and the irradiation time of the radiation 20, it is possible to adjust the mAs value by adjusting only one of the tube current or the irradiation time. Consequently, according to the present embodiment, the console 14 is capable of adjusting each of the tube voltage, the tube current, the irradiation time for the radiation 20, and the estimated AGD.

The present invention is not limited to the embodiment described above. Various changes and modifications can freely be made to the invention without departing from the scope and spirit of the invention.

The invention claimed is:

1. A radiographic image capturing system for carrying out a radiographic image capturing process by setting a tube voltage of a radiation source, an mAs value, types of a target and a filter that make up the radiation source, and information concerning a subject, as image capturing conditions, by an image capturing condition setting section, thereafter applying radiation from the radiation source to the subject according to the image capturing conditions, and converting radiation that has passed through the subject into a radiographic image by a radiation detector, the radiographic image capturing system comprising:

an estimated exposure dose calculator configured to calculate an estimated exposure dose representing an estimated value of a dose to which the subject will be exposed by applying radiation to the subject, on basis of the image capturing conditions after the image capturing conditions have been set and before the radiographic image capturing process is carried out;

an exposure dose output unit configured to output, to outside, the estimated exposure dose that has been calculated;

an image capturing condition adjuster configured to adjust the image capturing condition;

an estimated exposure dose adjuster configured to adjust the estimated exposure dose: and a table representing a relationship between estimated exposed doses, tube voltages, and mAs values, wherein the image capturing condition adjuster, in a state where the tube voltage is set to a fixed value, refers to the table, and adjusts the image capturing conditions by specifying the mAs value depending on the estimated exposure dose calculated by the estimated exposure dose calculator, or by specifying an mAs value depending on the estimated exposure dose adjusted by the estimated exposure dose adjuster.

2. The radiographic image capturing system according to claim 1, wherein the exposure dose output unit outputs the estimated exposure dose that has been adjusted by the estimated exposure dose adjuster.

3. The radiographic image capturing system according to claim 1, wherein the exposure dose output unit comprises a display unit configured to display the estimated exposure dose and the image capturing conditions.

4. The radiographic image capturing system according to claim 1, further comprising:

a radiographic image capturing apparatus including the radiation source and the radiation detector; and a control apparatus configured to control the radiographic image capturing apparatus, the control apparatus including the image capturing condition setting section, the estimated exposure dose calculator, and the exposure dose output unit, wherein the radiographic image capturing apparatus further includes an image capturing table on which a breast of the subject is placed, the image capturing table housing the radiation detector therein, a compression member configured to compress the breast by displacement of the compression member toward the image capturing table, and a compressed thickness measurement unit configured to measure a thickness of the breast that is compressed by the compression member, and wherein:

the radiation source applies radiation to the compressed breast;

the radiation detector converts radiation that has passed through the breast into the radiographic image;

among the image capturing conditions, the information concerning the subject represents the thickness of the breast of the subject; and the estimated exposure dose represents an estimated value of an average mammary gland dose applied to the breast.

5. A radiographic image capturing method for carrying out a radiographic image capturing process by setting a tube voltage of a radiation source, an mAs value, types of a target and a filter that make up the radiation source, and information concerning a subject, as image capturing conditions, thereafter applying radiation from the radiation source to the subject according to the image capturing conditions, and converting radiation that has passed through the subject into a radiographic image by a radiation detector, the method comprising:

a first step of calculating an estimated exposure dose representing an estimated value of a dose to which the subject will be exposed by applying radiation to the subject, on basis of the image capturing conditions after the image capturing conditions have been set and before the radiographic image capturing process is carried out;

a second step of outputting, to outside, the estimated exposure dose that has been calculated; and a third step of adjusting an image capturing condition, wherein in the third step, in a state where the tube voltage is set to a fixed value, a table representing a relationship between estimated exposure doses, tube voltages, and mAs values is referred to, and the image capturing conditions are adjusted by specifying an mAs value depending on the estimated exposure dose calculated, or by adjusting the estimated exposure dose and specifying an mAs value depending on the estimated exposure dose adjusted.

6. A non-transitory recording medium storing therein a program that enables a computer to function as:

an image capturing condition setting section configured to set a tube voltage of a radiation source, an mAs value, types of a target and a filter that make up the radiation source, and information concerning a subject, as image capturing conditions;

an estimated exposure dose calculator configured to calculate an estimated exposure dose representing an estimated value of a dose to which the subject will be exposed by applying radiation to the subject, on basis of the image capturing conditions before a radiographic image capturing process is carried out for applying radiation from the radiation source to the subject according to the image capturing conditions after the image capturing conditions have been set, and converting radiation that has passed through the subject into a radiographic image by a radiation detector;

an estimated exposure dose output unit configured to output, to outside, the estimated exposure dose that has been calculated;

an image capturing condition adjuster configured to adjust the image capturing conditions:

an estimated exposure dose adjuster configured to adjust the estimated exposure dose; and a table representing a relationship between estimated exposure doses, tube voltages, and mAs values, wherein the image capturing condition adjuster, in a state where the tube voltage is set to a fixed value, refers to the table, and adjusts the image capturing conditions by specifying the mAs value depending on the estimated exposure dose calculated by the estimated exposure dose calculator, or by specifying an mAs value depending on the estimated exposure dose adjusted by the estimated exposure dose adjuster.

* * * * *